United States Patent [19]

Sarstedt

[11] Patent Number: 4,588,556
[45] Date of Patent: May 13, 1986

[54] ARRANGEMENT FOR PLACING A SEPARATING GEL BETWEEN TWO PHASES LOCATED IN A SAMPLE TUBE

[75] Inventor: Walter Sarstedt, Nümbrecht-Rommelsdorf, Fed. Rep. of Germany

[73] Assignee: Walter Sarstedt Kunststoff-Spritzgusswerk, Rommelsdorf, Fed. Rep. of Germany

[21] Appl. No.: 676,329

[22] Filed: Nov. 29, 1984

[30] Foreign Application Priority Data

Dec. 5, 1983 [DE] Fed. Rep. of Germany ....... 3343887

[51] Int. Cl.⁴ .............................................. B01L 11/00
[52] U.S. Cl. .................................... 422/101; 210/359; 210/516; 210/927
[58] Field of Search ................. 422/101; 210/516, 927, 210/359

[56] References Cited

U.S. PATENT DOCUMENTS

| | | |
|---|---|---|
| 3,894,951 | 7/1975 | Ayres .............................. 210/516 X |
| 3,901,219 | 8/1975 | Kay .................................. 210/927 X |
| 3,931,010 | 1/1976 | Ayres et al. ..................... 210/516 X |
| 4,046,699 | 9/1977 | Zine ................................. 210/516 |
| 4,269,718 | 5/1981 | Persidsky ........................ 210/927 X |
| 4,295,974 | 10/1981 | Cornell ............................. 422/101 X |
| 4,417,981 | 11/1983 | Nugent ............................ 210/927 X |
| 4,425,235 | 1/1984 | Cornell et al. ................... 422/101 X |
| 4,425,320 | 1/1984 | Perry et al. ...................... 422/101 X |
| 4,486,315 | 12/1984 | Teipel ............................... 422/101 X |

Primary Examiner—Robert Lindsay
Attorney, Agent, or Firm—Townsend & Townsend

[57] ABSTRACT

Figure 3:
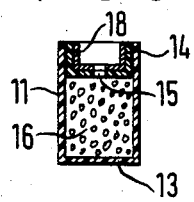

An arrangement for placing a separating gel between two phases of different specific gravity located in a sample tube has a container (11) in which a separating gel (16) is accommodated. The container (11) which can be inserted into the sample tube up to the bottom thereof has a closed base (13) and a lid (14) at the top which can be displaced within the container in the manner of a piston. The lid is provided with at least one discharge opening (15) which is small relative to the area of the lid. The specific gravity of the lid (14) is greater than that of the separating gel (15) (FIG 3).

20 Claims, 8 Drawing Figures

ARRANGEMENT FOR PLACING A SEPARATING GEL BETWEEN TWO PHASES LOCATED IN A SAMPLE TUBE

The invention relates to an arrangement for placing a separating gel between two phases of different specific gravity which initially form a dispersion or suspension and which are located in a sample tube which is open at the top, or to be opened at the top, and closed at the bottom, there being a container in which the separating gel, which has a specific gravity lying between the specific gravities of the two phases, is housed and which has at least one discharge opening for the separating gel which opens into the interior of the sample tube.

Such arrangements are principally used for the investigation of a blood in which, after the addition of a coagulating agent into a sample tube containing the blood, the blood cake which forms the one phase is separated from the serum which represents the other phase by centrifuging. The separating gel has approximately the specific gravity of the blood so that it places itself during the separation of the blood cake of higher specific gravity from the blood serum of lower specific gravity between these two phases, and thus forms a troublefree separating layer. Generally the invention relates to dispersions or suspensions in which a liquid or solid substance of higher specific gravity is mixed with a liquid of a lower specific gravity.

Various arrangements are known in which a thixotropic separating gel can be place by centrifuging between the two phases of different specific gravity.

In one known arrangement of the initially named kind (German Offenlegungsschrift DE-OS 23 40 199) a small container having an opening at the bottom is placed on the sample tube containing the blood in the manner of a plug. During centrifuging the separating gel slowly emerges from the container and places itself between the two separated phases.

In another known solution (German Offenlegungsschrift DE-OS No. 23 59 670) the separating gel is arranged at the base of the sample tube, from which it rises during the course of centrifuging the blood which is placed above it, as a result of the intermediate specific gravity, and places itself over the heavier of the two phases which have been separated from one another. In order to facilitate the rising of the separating gel during centrifuging a displacement body can also be arranged on the separating gel which displaces the gel during centrifuging and allows it to flow upwardly through a channel provided in the displacement body or at its external periphery (German laying open prints DE-OS No. 25 09 145, DE-OS No. 25 45 749, DE-OS No. 30 14 986).

The arrangement with the container placed at the top has the disadvantage that the container can only be placed into the sample tube after the dispersion has been introduced. This is particularly disadvantageous with sample tubes which form an element of a blood extraction device and contain a blood extraction piston. The latter is located prior to blood extraction in an advanced position so that the container with the separating gel can only be placed at the top after blood extraction when the piston is retracted and the closure cap is unscrewed.

The arrangement of the separating gel at the base of the sample tube at the outset cannot be used at all with sample tubes containing a blood extraction piston, and is also disadvantageous with other sample tubes because these must be provided with the separating gel at the outset, so that the user no longer has any choice whether he will work with or without the separating gel. The object of the present invention is to provide an arrangement of the initially named kind which can be arranged in the sample tube prior to the extraction of blood, even in blood extraction devices which are provided with sample tubes having a blood extraction piston and a closure cap, and which can also be arranged in other sample tubes which do not contain a separating gel and which are also not specially constructed to accommodate the same but which permit the introduction of the separating gel prior to filling with the dispersion.

In order to solve this problem the invention provides that the container which can be inserted into the sample tube up to the bottom thereof has a closed base, and a lid at the top which can be displaced within the container in the manner of a piston and which has at least one opening which is small relative to the area of the lid; and that the specific gravity of the lid is greater than that of the separating gel.

The thought underlying the invention is thus to be seen in the fact that a small and special container with a base which can be inserted into the sample tube up to the bottom thereof is used for the placement of the separating gel, with the container however being not completely open at the top but instead having a lid there which is provided with only one or several relatively small openings, so that the separating gel cannot simply flow away during normal handling, but only when larger centrifugal forces occur during centrifuging and the lid is hereby gradually moved to the bottom, whereby the separating gel is pressed outwardly through the openings. During transport, during storage and during normal handling escape of the gel need not however be feared because the openings are made appropriately small. Moreover, the container of the invention can be additionally and straightforwardly hermetically sealed by an adhesive foil or the like which can be peeled away.

At the place of use it is possible to decide from case to case whether one wishes to operate during the blood investigation with a separating gel or not. If required one merely needs to insert the container with the separating gel, in accordance with the invention, into the sample tube which preferably takes place prior to introduction of the blood, but which can however also take place afterwards. The arrangement in accordance with the invention is thus capable of very universal usage.

As a result of the construction of the invention a troublefree separating layer is formed by the separating gel during centrifuging. By suitable choice of the size of the openings in the lid it is possible to straightforwardly control the time at which the separating layer forms during centrifuging. The smaller the openings are made the longer it takes until the separating layer is formed. Smaller openings do however make it possible to effectively avoid premature escape of the separating gel.

The container preferably has a right-cylindrical shape so that it fits ideally into cylindrical sample tubes. Its diameter is smaller than the internal diameter of the sample tubes so that it can be inserted there effortlessly and without friction.

Although a simple disk can be used the lid is preferably of pot-shape so that a cylindrical edge projects axially away from the disk part and ensures troublefree sliding of the lid in the cylindrical container without the danger of tilting. The edge should project axially outwardly from the disk part so that the disk part can be displaced to the base of the container. Troublefree formation of the separating layer is ensured when the lid has a central discharge opening.

It is however also possible for the lid to have one or more recesses at the edge which form the discharge openings with the wall of the container.

The container can be fixed to the base of the sample tube in order to ensure troublefree positioning independently of its specific gravity.

If a sample tube is used having a blood extraction piston inserted therein then the container should be associated with the piston which preferably takes place by making it insertable into a recess in the front side of the piston, and indeed preferably when the piston is in its not yet retracted position at the front end of the sample tube. The recess is expediently the recess which is in any event present at the front side of a pot-like piston.

The container is preferably securable in the recess of the piston.

To the extent that a blood extraction device of this kind is intended to accommodate a separating gel from the outset the container can also be in one piece with the piston. When compared with the simple introduction nof the separating gel into the recess of a pot-like piston this embodiment has however the advantage that, on the one hand, premature escape of the separating gel is avoided as a result of the placement of the piston-like lid on or in the container and, on the other hand, that complete escape of the separating gel out of the container is ensured when the lid is pressed to its base.

It is of especial advantage, in particular with the above named embodiment, when the outwardly facing surfaces of the lid are provided with a substance which promotes coagulation. When using a separating gel the addition of a substance which promotes coagulation is namely also generally necessary and the lid provided in accordance with the invention can now be used for introduction of the coagulation promoting substance in addition to its function as a gel displacement means. In this embodiment the lid thus also effects a double function.

In accordance with a first embodiment the substance which promotes coagulation is applied as a coating to the outwardly directed surfaces of the lid. With a lid of pot-like shape the substance promoting coagulation can also be placed therein, for example as a liquid or powder.

The specific gravity of the container with the lid is preferably greater than that of the dispersion or suspension because it is then ensured, independently of any fixing of the container, that the container with the lid does not float during centrifuging or during handling.

Since, in accordance with the invention, the lid should be of greater specific gravity than the separating gel, both the container on its own and the separating gel expediently have approximately the same specific gravity as the dispersion or suspension.

Figure 2:
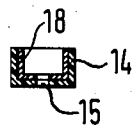
Figure 1:
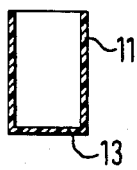
Figure 4:
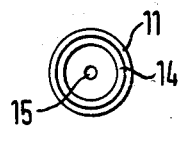
Figure 5:
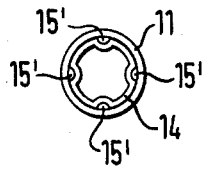
Figure 6:
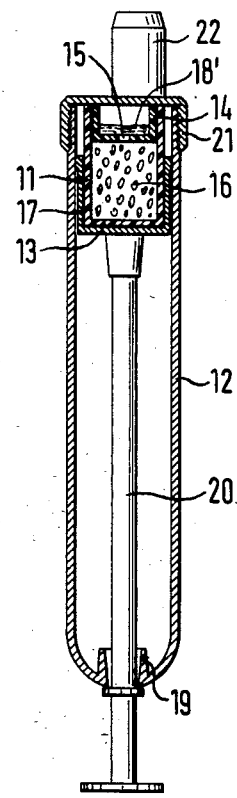
Figure 7:
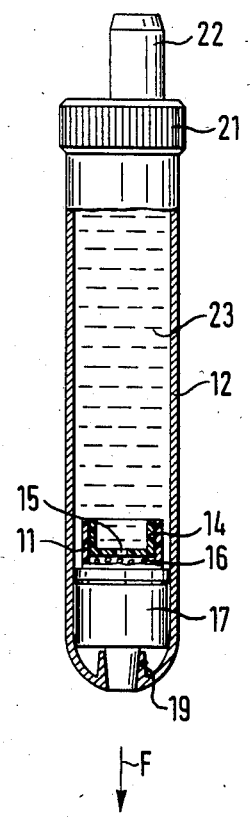
Figure 8:
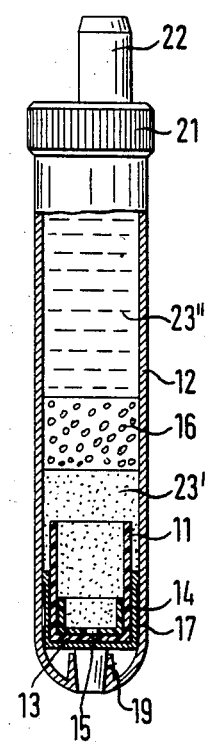

The invention will now be described in the following by way of example and with reference to the drawings in which are shown:

FIG. 1 a central vertical section of a container used in the arrangement of the invention, FIG. 2 a corresponding central vertical section of the piston-like lid which belongs thereto, FIG. 3 a corresponding central vertical section of the container of FIG. 1 with the lid of FIG. 2 inserted therein and filled with separating gel, FIG. 4 a plan view of the article of FIG. 3, FIG. 5 a corresponding plan view of a modified embodiment, FIG. 6 a partially sectioned side view of a blood extraction device equipped with the arrangement of the invention and with the piston advanced, FIG. 7 a partially sectioned side view analogous to FIG. 6 with the piston retracted and the piston rod removed together with the drawn in blood, and FIG. 8 a partially sectioned side view analogous to FIGS. 6 and 7 of a blood extraction device equipped with the arrangement of the invention after centrifuging.

As seen in FIGS. 1 to 4 a right-cylindrical container 11 which has a closed flat base 13 and which is open in throughgoing manner at the top is used for filling or accommodating the separating gel. As seen in FIG. 3 the separating gel 16 is filled into this container up to approximately ¾ of its height. A pot-like lid 14 (FIGS. 2, 3) which comprises a disk-like part having a small central discharge opening 15 and a cylindrical edge which projects upwardly away from the disk-like part, is inserted into the container 11 at the top. The diameter of the lid 14 is selected so that it is displaceable inside the container 11 in the manner of a piston, with the interior of the container however essentially only being in communication with the external space via the central opening 15.

As seen in FIG. 5 recesses 15' can also be provided at the edges of the lid 14 in order to produce this communication, with the recesses together with the inner wall of the container 11 representing the discharge openings between the inner chamber of the container and the surroundings.

After the separating gel 16 has been inserted into the container 11 the lid 14 is placed thereon and displaced into the position which can be seen from FIG. 3 in which the lid 14 is flush with the upper edge of the container 11. In order to hermetically seal the arrangement so formed for transport and storage against the outside environment an adhesive foil, which can be simply peeled off prior to use, can for example be placed at the top.

Both the container 11 and also the lid 14 can be straightforwardly manufactured as injection-molded parts in synthetic material. The specific gravity of the entire assembly consisting of container 11 and lid 14 must be higher than the specific gravity of the dispersion or suspension, which in a blood investigation arrangement consists of blood. The specific gravity of blood amounts to approximately 1.05 g/cm$^3$. This choice of the specific gravity of the mentioned assembly is important because the container 11 with the lid 14 must not float after blood extraction or during centrifuging.

Furthermore, it is important that the lid 14 has a greater specific gravity than the separating gel 16, the specific gravity of which corresponds substantially to that of the unseparated blood. The container 11 is preferably manufactured of polystyrol and should have a specific gravity approximately the same as that of the blood or of the separating gel (ca. 1.05 g/cm$^3$). The lid 14 should have a substantially higher specific gravity, of for example over 1.1 g/cm$^3$ in order to form a troublefree separating layer.

As seen in FIG. 6 a right-cylindrical sample tube 12 has a through-opening 19 for a piston rod 20 at the lower end, with the piston rod leading to a piston 17 arranged within the sample tube. At the top the sample tube 12 is closed by a closure cap 21 from which a projection 22 projects which can be punctured by a cannula sharpened at both ends. The cannula is not shown in the drawing.

By unscrewing the closure cap the container 11 of the invention together with the gel 16 and the lid 14 can be inserted from the front into the pot-like piston 17 which is located in the advanced position as seen in FIG. 6. The container 11 can be fixedly clamped in the piston 17 by suitably dimensioning the container, this is however not essential. The closure cap 21 is then subsequently screwed on again so that the blood extraction device adopts the position shown in FIG. 6. the container 11 can however fundamentally also be inserted during manufacture.

A cannula is now mounted on the projection 22 and punctures the closure plug located in the projection 22, so that blood can be extracted from a patient after insertion of the cannula into a vein and retraction of the piston 17. After the taking of the blood the cannula is removed from the projection 22 and the piston rod 20 from the piston 17. This state of the blood extraction device is illustrated in FIG. 7. The blood 23 is located above the piston 17 and above the container 11 of the invention with the lid 14. In this state the blood extraction device is introduced into a centrifuge, which is not shown in the drawing, in which centrifugal forces are applied to the sample tube 23 in the direction of the arrow F. The centrifugal forces press the lid 14, steadily to the base 13 of the container 11 as a result of the appropriately selected specific gravity, with the separating gel 16 emerging through the central discharge opening 15 or the lateral discharge openings 15' (FIG. 5) and placing itself in the manner shown in FIG. 8 between the blood cake 23' which settles out at the bottom and the upwardly rising blood serum 23'.

It is important for the invention that the discharge openings 15, 15' are not made too large because otherwise the separating gel 16 could escape too early or in uncontrolled manner from the container 11.

A substantial advantage of the arrangement of the invention lies in the fact that the separating gel cartridge consisting of the container 11, the separating gel 16 and the lid 14 can be manufactured and made ready completely separately from the sample tube or the blood extraction device. The separating gel cartridge can thus be stored and delivered entirely separately from the sample tubes and blood extraction devices.

With the aid of the separating gel cartridge of the invention any desired sample tubes having internal dimensions which are sufficiently large that they permit the insertion of the separating gel cartridge of the invention can be selectively provided with a separating gel. Handling is entirely without problem and there is no danger that the operator comes into contact with the separating gel in one way or another. By changing the size and the arrangement of the discharge openings 15, 15' in the lid 14 it is possible, to influence the time at which the separating gel escapes from the separating gel cartridge in simple manner. A further particular advantage of the invention lies in the fact, as seen in FIGS. 2, 3 and 6, that a coagulation promoting substance can be associated with the surfaces of the lid 14 which communicate with the environment. As seen in FIGS. 2 and 3 the outwardly directed surfaces of the lid 14 are provided with a coating 18 of a substance which promotes coagulation. In the embodiment of FIG. 6 a substance 18' which promotes coagulation is introduced into the interior of the pot-like lid 14.

The arrangement of the invention can be used with particular advantage with blood extraction devices in accordance with the suction piston principle, in as much as the use of a separating gel is possible without subsequent manipulation after the taking of blood. In particular, no special container has to be subsequently mounted in order to dispense a flow of the gel.

During centrifuging the blood cake 23' (FIG. 8) and the lid 14, which preferably has a higher specific gravity than the blood cake, press on the separating gel 16 and on the container fixed at the base of the pot-like piston 17, whereby the separating gel can escape through the central opening in the lid 14 and finally forms the separating layer of gel 16 shown in FIG. 8.

It is furthermore advantageous that the closure cap 21 does not have to be taken off prior to centrifuging.

If the discharge opening 15 is centrally arranged then the cross-sectional area of the opening amounts to ca. 1 to 2% of the total lid area. If the discharge opening 15' is arranged at the edge of the lid then the area of the opening can amount to up to 15% of the total lid area. For the final choice of the size of the discharge opening the specific gravity and the thickness of the base, i.e. the ratio of diameter to length of the exit passage, plays a substantial role.

I claim:
1. An apparatus for placing a separating gel (16) between two phases of different specific gravity which initially form a dispersion or a suspension in a sample tube (12), said sample tube having a closed bottom and an open or openable top, comprising:
    a container (11) adapted to hold said separating gel, said container having a closed bottom and an open top and being shaped such that said container can be inserted into said sample tube up to the bottom of said sample tube; and
    a lid (14) displaced within said container and slidable up and down inside said container, said lid having at least one opening (15, 15') which is small relative to the area of said lid, said lid having a specific gravity greater than the specific gravity of said separating gel.

2. An apparatus in accordance with claim 1, wherein said container (11) has a right-cylindrical shape.

3. An apparatus in accordance with claim 1, wherein said lid (14) has the form of a pot which is open at the top.

4. An apparatus in accordance with claim 1, wherein said opening is at the center of said lid.

5. An apparatus in accordance with claim 1, wherein said lid (14) has one or more recesses (15') at an edge of said lid, said recesses forming discharge openings bounded by said lid and an interior wall of said container.

6. An apparatus in accordance with claim 1, wherein said container (11) is adapted to be fixed to the base of the sample tube (12).

7. An apparatus in accordance with claim 1 further comprising a blood extraction device having a piston arranged in said sample tube, said piston (17) being retractable to a base of said sample tube, said container (11) being arranged to rest on said piston.

8. An apparatus in accordance with claim 7, wherein said container (11) has an exterior surface shaped to insert into a recess in the front side of said piston (17).

9. An apparatus in accordance with claim 8, wherein said recess is formed by a pot-like shape of said piston (17).

10. An apparatus in accordance with claim 7, further comprising means for coupling said container into said recess.

11. An apparatus in accordance with claim 7, wherein said container and said piston are one piece.

12. An apparatus in accordance with claim 1, wherein the specific weight of a unit consisting of said container (11) and said lid (14) is greater than the specific weight of said dispersion or suspension.

13. An apparatus in accordance with claim 12 wherein said container (11) and said separating gel (16) have approximately the specific weight of said dispersion or suspension.

14. An apparatus in accordance with claim 4, wherein the surface area taken up by said opening (15) amounts to 1 to 2% of the total surface of said lid.

15. An apparatus in accordance with claim 5, wherein the surface area taken up by said discharge openings (15') amounts to 5 to 15% of the total surface of said lid.

16. An apparatus in accordance with claim 1, characterised in that the outwardly facing surfaces of the lid (14) are provided with a substance (18, 18') which promotes coagulation.

17. An apparatus in accordance with claim 16, characterised in that the substance (18) which promotes coagulation is applied as a coating to the outwardly facing surfaces of the lid (14).

18. An apparatus in accordance with claim 3, characterised in that a substance (18') which promotes coagulation is present in the pot-like lid (14).

19. An apparatus comprising:
- a sample tube (12) having a closed bottom and an open or openable top;
- a container (11) having a closed bottom and an open top and being shaped such that said container can be inserted into said sample tube up to the bottom of said sample tube;
- a separating gel disposed within said container; and
- a lid (14) displaced within said container and slidable up and down inside said container, said lid having at least one opening (15, 15') which is small relative to the area of said lid, said lid having a specific gravity greater than the specific gravity of said separating gel.

20. An apparatus separating two phases of different specific gravity which initially form a dispersion or suspension in a sample tube (12), said sample tube having a closed bottom and an open or openable top, comprising:
- a container (11) having a closed bottom and an open top and being shaped such that said container can be inserted into said sample tube up to the bottom of said sample tube;
- a separating gel disposed within said container; and
- a lid (14) displaced within said container and slidable up and down inside end container, said lid having at least one opening (15, 15') which is small relative to the area of said lid, said lid having a specific gravity greater than the specific gravity of said separating gel.

* * * * *